(12) United States Patent
DiFoggio et al.

(10) Patent No.: US 9,366,133 B2
(45) Date of Patent: Jun. 14, 2016

(54) ACOUSTIC STANDOFF AND MUD VELOCITY USING A STEPPED TRANSMITTER

(71) Applicants: Rocco DiFoggio, Houston, TX (US); Wei Han, Sugar Land, TX (US)

(72) Inventors: Rocco DiFoggio, Houston, TX (US); Wei Han, Sugar Land, TX (US)

(73) Assignee: BAKER HUGHES INCORPORATED, Houston, TX (US)

( * ) Notice: Subject to any disclaimer, the term of this patent is extended or adjusted under 35 U.S.C. 154(b) by 218 days.

(21) Appl. No.: 14/278,839

(22) Filed: May 15, 2014

(65) Prior Publication Data

US 2014/0247694 A1 Sep. 4, 2014

Related U.S. Application Data

(63) Continuation-in-part of application No. 13/401,503, filed on Feb. 21, 2012, now Pat. No. 9,109,433.

(51) Int. Cl.
*G01V 1/44* (2006.01)
*E21B 47/10* (2012.01)
(Continued)

(52) U.S. Cl.
CPC ............ *E21B 47/101* (2013.01); *G01F 23/247* (2013.01); *G01F 23/2961* (2013.01); *G01N 29/024* (2013.01); *G01N 29/028* (2013.01); *G01N 29/4418* (2013.01); *G01N 2291/02818* (2013.01); *G01N 2291/02836* (2013.01); *G01N 2291/045* (2013.01); *G01V 1/50* (2013.01)

(58) Field of Classification Search
CPC .. E21B 47/101; G01N 29/024; G01N 29/028; G01N 29/4418; G01N 2291/02818; G01N 2291/02836; G01N 2291/045; G01F 23/247; G01F 23/2961; G01V 1/50

USPC .......................................................... 367/86
See application file for complete search history.

(56) References Cited

U.S. PATENT DOCUMENTS 2,244,484 A 6/1941 Beers
3,776,032 A 12/1973 Vogel
(Continued)

FOREIGN PATENT DOCUMENTS

WO WO9850680 A2 11/1998

OTHER PUBLICATIONS

Bulloch, T. E.; The Investigation of Fluid Properties and Seismic Attributes for Reservoir Characterization, Thesis for degree of Master of Science in Geological Engineering, Michigan Technological University, 1999, pp. A1-A6.
(Continued)

*Primary Examiner* — Daniel L Murphy
(74) *Attorney, Agent, or Firm* — Cantor Colburn LLP

(57) ABSTRACT

A system, apparatus and method for determining an acoustic property of a fluid in a wellbore is disclosed. A faceplate is placed in the wellbore with a stepped surface of the faceplate in contact with the fluid. The stepped surface includes a non-stepped face and a stepped face. A first portion of an acoustic pulse passes from the faceplate into the fluid via the non-stepped face and a second portion of the acoustic pulse passes from the faceplate into the fluid via the stepped face. A first reflected acoustic pulse related to the first portion of the acoustic pulse is received. A second reflected acoustic pulse related to the second portion of the acoustic pulse is received. A measurement of the first reflected acoustic pulse and a measurement of the second reflected pulse are used to determine the acoustic property of the fluid in the wellbore.

20 Claims, 4 Drawing Sheets

(51) Int. Cl.
*G01N 29/024* (2006.01)
*G01N 29/028* (2006.01)
*G01N 29/44* (2006.01)
*G01F 23/24* (2006.01)
*G01F 23/296* (2006.01)
*G01V 1/50* (2006.01)

(56) References Cited

U.S. PATENT DOCUMENTS

| | | | |
|---|---|---|---|
| 4,022,055 A * | 5/1977 | Flournoy | G01B 17/02 367/141 |
| 4,208,906 A | 6/1980 | Roberts, Jr. | |
| 4,273,212 A | 6/1981 | Dorr et al. | |
| 4,412,130 A | 10/1983 | Winters | |
| 4,492,865 A | 1/1985 | Murphy et al. | |
| 4,571,693 A | 2/1986 | Birchak et al. | |
| 4,619,267 A | 10/1986 | Lannuzel et al. | |
| 4,733,232 A | 3/1988 | Grosso | |
| 4,769,793 A | 9/1988 | Kniest et al. | |
| 4,938,066 A | 7/1990 | Dorr | |
| 5,130,950 A | 7/1992 | Orban et al. | |
| 5,163,029 A | 11/1992 | Bryant et al. | |
| 5,275,040 A | 1/1994 | Codazzi | |
| 5,635,626 A | 6/1997 | Hammond et al. | |
| 5,741,962 A | 4/1998 | Birchak et al. | |
| 6,029,507 A | 2/2000 | Faber et al. | |
| 6,032,516 A | 3/2000 | Takahashi et al. | |
| 6,047,602 A * | 4/2000 | Lynnworth | G01F 1/662 73/632 |
| 6,050,141 A | 4/2000 | Tello et al. | |
| 6,176,323 B1 | 1/2001 | Weirich et al. | |
| 6,205,848 B1 | 3/2001 | Faber et al. | |
| 6,208,586 B1 | 3/2001 | Rorden et al. | |
| 6,250,137 B1 | 6/2001 | Takahashi et al. | |
| 6,618,322 B1 * | 9/2003 | Georgi | G01V 1/46 181/105 |
| 6,634,214 B1 | 10/2003 | Thurston et al. | |
| 6,648,083 B2 | 11/2003 | Evans et al. | |
| 6,672,163 B2 | 1/2004 | Han et al. | |
| 6,768,106 B2 | 7/2004 | Gzara et al. | |
| 6,817,229 B2 | 11/2004 | Han et al. | |
| 6,829,947 B2 | 12/2004 | Han et al. | |
| 6,957,572 B1 | 10/2005 | Wu | |
| 7,024,917 B2 | 4/2006 | DiFoggio | |
| 7,334,651 B2 | 2/2008 | Wu | |
| 2002/0100327 A1 | 8/2002 | Kersey et al. | |
| 2002/0117003 A1 | 8/2002 | Banno et al. | |
| 2002/0178787 A1 | 12/2002 | Matsiev et al. | |
| 2002/0178805 A1 | 12/2002 | DiFoggio et al. | |
| 2002/0184940 A1 | 12/2002 | Storm, Jr. et al. | |
| 2002/0189367 A1 | 12/2002 | Gomm et al. | |
| 2002/0194906 A1 | 12/2002 | Goodwin et al. | |
| 2003/0029241 A1 | 2/2003 | Mandal | |
| 2003/0029242 A1 | 2/2003 | Yaralioglu et al. | |
| 2003/0051533 A1 | 3/2003 | James et al. | |
| 2003/0101819 A1 | 6/2003 | Mutz et al. | |
| 2003/0144746 A1 | 7/2003 | Hsiung et al. | |
| 2003/0150262 A1 | 8/2003 | Han et al. | |
| 2003/0172734 A1 | 9/2003 | Greenwood | |
| 2003/0209066 A1 | 11/2003 | Goodwin | |
| 2003/0220742 A1 | 11/2003 | Niedermayr et al. | |
| 2004/0007058 A1 | 1/2004 | Rylander et al. | |
| 2004/0020294 A1 | 2/2004 | Buckin | |
| 2004/0040746 A1 | 3/2004 | Niedermayr et al. | |
| 2004/0060345 A1 | 4/2004 | Eggen et al. | |
| 2004/0095847 A1 | 5/2004 | Hassan et al. | |
| 2004/0173017 A1 | 9/2004 | O'Brien | |
| 2004/0194539 A1 | 10/2004 | Gysling | |
| 2004/0216515 A1 | 11/2004 | Yakhno et al. | |
| 2004/0236512 A1 | 11/2004 | DiFoggio et al. | |
| 2005/0103097 A1 | 5/2005 | Faltum et al. | |
| 2005/0149277 A1 | 7/2005 | Bailey et al. | |
| 2005/0212869 A1 | 9/2005 | Ellson et al. | |
| 2005/0223808 A1 | 10/2005 | Myers et al. | |
| 2005/0252294 A1 | 11/2005 | Ariav | |
| 2005/0268703 A1 | 12/2005 | Funck et al. | |
| 2007/0022803 A1 | 2/2007 | DiFoggio et al. | |
| 2008/0047337 A1 | 2/2008 | Chemali et al. | |
| 2009/0173150 A1 | 7/2009 | DiFoggio et al. | |
| 2009/0272580 A1 | 11/2009 | Dolman et al. | |
| 2010/0315900 A1 | 12/2010 | Difoggio et al. | |

OTHER PUBLICATIONS

Doyle, E.F. et al.; "Plan for Surprises: Pore Pressure Challenges during the drilling of a Deepwater Exploration Well in mid-winter in Norway," SPE/IADC 79848, SPE/IADC Drilling Conference, Amsterdam, The Netherlands, Feb. 19-21, 2003, pp. 1-8.

Guyod, Hubert; "Temperature Well Logging," Oil Weekly, Well Logging, Part 6, 1946, pp. 40-44.

Havira, R. M.; "Ultrasonic Cement Bond Evaluation," Paper N, SPWLA Twenty-Third Annual Logging Symposium, Jul. 6-9, 1982, pp. 1-11.

Honarvar, F. et al.; Reference wavelets used for deconvolution of ultrasonic time-of-flight diffraction (ToFD) signals, 17th World Conference on Nondestructive Testing, Oct. 25-28, 2008, Shanghai, China, pp. 1-9.

International Search Report and Written Opinion dated Jun. 12, 2013 for International Application No. PCT/US2013/026832, pp. 1-15.

Kading, Horace W. et al.; "Temperature Surveys: The Art of Interpretation," Am. Pet. Inst., Pub.; (United States); Journal vol. 906-14-N; Conference; API southwestern district product division spring meeting, Luddbock, Texas, USA, Mar. 12, 1969, pp. 1-20.

Mohanty, Sitakanta; "Effect of Multiphase Fluid Saturation on the Thermal Conductivity of Geologic Media," J. Phys. D. Appl. Phys., 30, No. 24 (Dec. 21, 1997), pp. L-80-L84.

Reservoir Characterization Instrument, RCI Instrument Modules, pamphlet from Baker Hughes, Copyright 2000 Baker Hughes Incorporated, pp. 7-1-7-28.

Savitzky, A. et al.; "Smoothing and Differentiation of Data by Simplified Least Squares Procedures," Analytical Chemistry, International Gas Chromatography Symposium, vol. 36, No. 8, Jul. 1964, pp. 1627-1639.

Weatherford, "HEL MWD System-Rapid Annular Temperature (RAT) Sensor," http://www.weatherford.com/weatherford/groups/web/documents/weatherfordcorp/wft104872.pdf, 2 sheets.

* cited by examiner

Case 1. $c_x > c_L$

Case 2. $c_x < c_L$

ACOUSTIC STANDOFF AND MUD VELOCITY USING A STEPPED TRANSMITTER

CROSS-REFERENCE TO RELATED APPLICATIONS

This application is a continuation-in-part of U.S. patent application Ser. No. 13/401,503, filed Feb. 21, 2012.

BACKGROUND OF THE DISCLOSURE

1. Field of the Disclosure

The present disclosure is related to testing of fluids in a wellbore and, in particular, to methods and apparatus for determining acoustic properties of fluids in the wellbore.

2. Description of the Related Art

Exploration for hydrocarbons commonly includes using a bottomhole assembly including a drill-bit for drilling a borehole in an earth formation. Drilling fluid or "mud" used in the drilling may vary in density or "mud weight" for a number of reasons. Such variations can result from changes in the quantity and density of cuttings (particles of formation); changes in the "mud program" at the surface, changes in temperature, etc. Variations in mud density also occur when gas or liquid enter the borehole from the formation. Such influx of formation fluids may likely be the result of formation overpressures or abnormally high pressures.

Pressure detection is useful in drilling operations. Not only does the drilling rate decrease with a high overbalance of mud pressure versus formation pressure, but also lost circulation and differential pressure sticking of the drill pipe can readily occur. More importantly, an underbalance of mud pressure versus formation pressure can cause a pressure "kick." A well may kick without forewarning. Balanced drilling techniques often require only a fine margin between effective pressure control and a threatened blowout. Additionally, there are situations where it is desired to maintain underbalance to avoid formation damage. Thus, there is a need to measure the properties of the borehole fluid downhole in order to detect, among other things, kicks and inflow of formation liquids.

SUMMARY OF THE DISCLOSURE

In one aspect, the present disclosure provides a method of determining an acoustic property of a fluid in a wellbore, the method including: placing a faceplate in the wellbore with a stepped surface of the faceplate in contact with the fluid, wherein the stepped surface includes a non-stepped face and a stepped face; transmitting an acoustic pulse through the faceplate into the fluid, wherein a first portion of the acoustic pulse passes from the faceplate into the fluid via the non-stepped face and a second portion of the acoustic pulse passes from the faceplate into the fluid via the stepped face; receiving a first reflected acoustic pulse related to the first portion of the acoustic pulse from a wellbore surface and a second reflected acoustic pulse related to the second portion of the acoustic pulse from the wellbore surface; obtaining a measurement of the first reflected acoustic pulse and a measurement of the second reflected pulse; and determining from the obtained measurements the acoustic property of the fluid in the wellbore.

In another aspect, the present disclosure provides an apparatus for determining an acoustic property of a fluid in a wellbore, the apparatus including: a faceplate having a stepped surface that includes a non-stepped face and a stepped face, wherein the stepped surface is coupled to the fluid in the wellbore; an acoustic transducer configured to transmit an acoustic signal to pass through the stepped surface of the faceplate into the fluid, wherein a first portion of the transmitted acoustic signal passes from the faceplate into the fluid via the non-stepped face and a second portion of the acoustic pulse passes from the faceplate into the fluid via the stepped face; and a processor configured to: receive measurements of a first reflected pulse related to reflection of the first portion of the transmitted acoustic signal from a wellbore surface a second reflected pulse related to reflection of the second portion of the transmitted acoustic signal from the wellbore surface, and determine the acoustic property of the fluid in the wellbore from the received measurements of the first reflected acoustic pulse and the second reflected acoustic pulse.

In yet another aspect, the present disclosure provides a system for determining an acoustic property of a fluid in a wellbore, the system including: a member disposed in the wellbore; a faceplate disposed on the member, the faceplate having a stepped surface coupled to the fluid in the wellbore, wherein the stepped surface includes a non-stepped face and a stepped face; an acoustic transducer configured to transmit an acoustic signal into the faceplate, wherein a first portion of the transmitted acoustic signal passes from the faceplate into the fluid through the non-stepped face and a second portion of the transmitted acoustic signal passes from the faceplate into the fluid through the stepped face, the acoustic transducer further configured to receive a first reflected acoustic signal related reflection of the first portion of the transmitted acoustic signal from a surface of the wellbore and a second reflected acoustic signal related to reflection of the second portion of the transmitted acoustic signal from the surface of the wellbore; and a processor configured to: receive measurements of the first reflected pulse and the second reflected pulse from the acoustic transducer, and determine the acoustic property of the fluid in the wellbore from the received measurements of the first reflected acoustic pulse and the second reflected acoustic pulse.

Examples of certain features of the apparatus and method disclosed herein are summarized rather broadly in order that the detailed description thereof that follows may be better understood. There are, of course, additional features of the apparatus and method disclosed hereinafter that will form the subject of the claims.

BRIEF DESCRIPTION OF THE DRAWINGS

For detailed understanding of the present disclosure, references should be made to the following detailed description, taken in conjunction with the accompanying drawings, in which like elements have been given like numerals and wherein.

DETAILED DESCRIPTION OF THE DISCLOSURE

Figure 1:
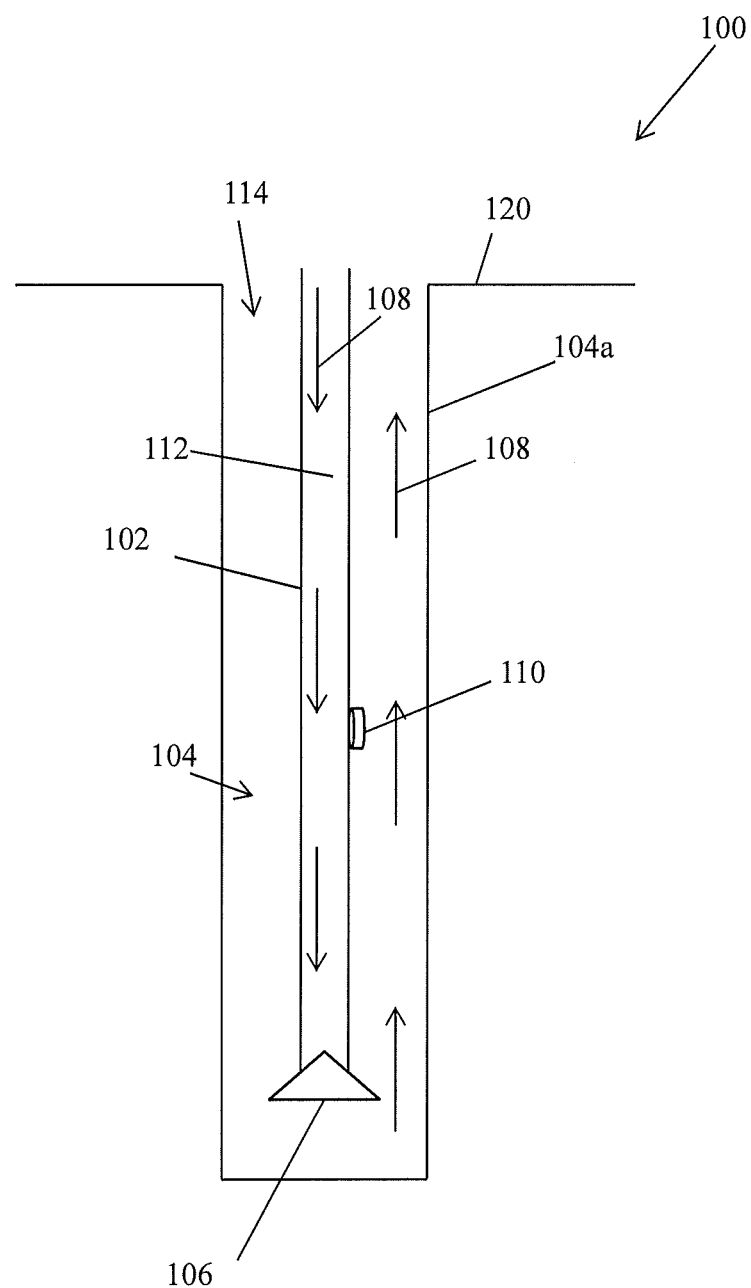
FIG. 1 shows an illustrative wellbore system suitable for determining an acoustic property of fluid in a wellbore in one embodiment of the present disclosure.

FIG. 1 shows an illustrative wellbore system 100 suitable for determining an acoustic property of fluid 108 in a wellbore 104 in one embodiment of the present disclosure. The wellbore system 100 includes a member 102 that extends from a surface location 120 into a borehole or wellbore 104. The wellbore 104 may be an open wellbore or a cased wellbore, in various embodiments. A surface 104a (also referred to herein as a "wellbore wall 104a") of the wellbore 104 may be a surface of a formation or an interior face of a casing (not shown) disposed in the wellbore 104. An annulus 114 is formed between the member 102 and the wellbore wall 104a. In one embodiment, the member 102 may be a drillstring that includes a drill bit 106 at a bottom end for drilling the wellbore 104. A fluid 108 such as a drilling mud may be pumped into the wellbore 104 through a bore 112 in the member 102 to exit the member 102 at the drill bit 106. The fluid 108 then travels back to the surface location 120 via the annulus 114. In the annulus 114, the fluid 108 may include drilling mud as well as formation fluids and/or formation gases. Determining properties of the fluid in the annulus 114 is useful in drilling operations. The member 102 includes a fluid testing apparatus 110 suitable for determining a property of the fluid 108 in the annulus 114 of the wellbore 104.

Figure 2:
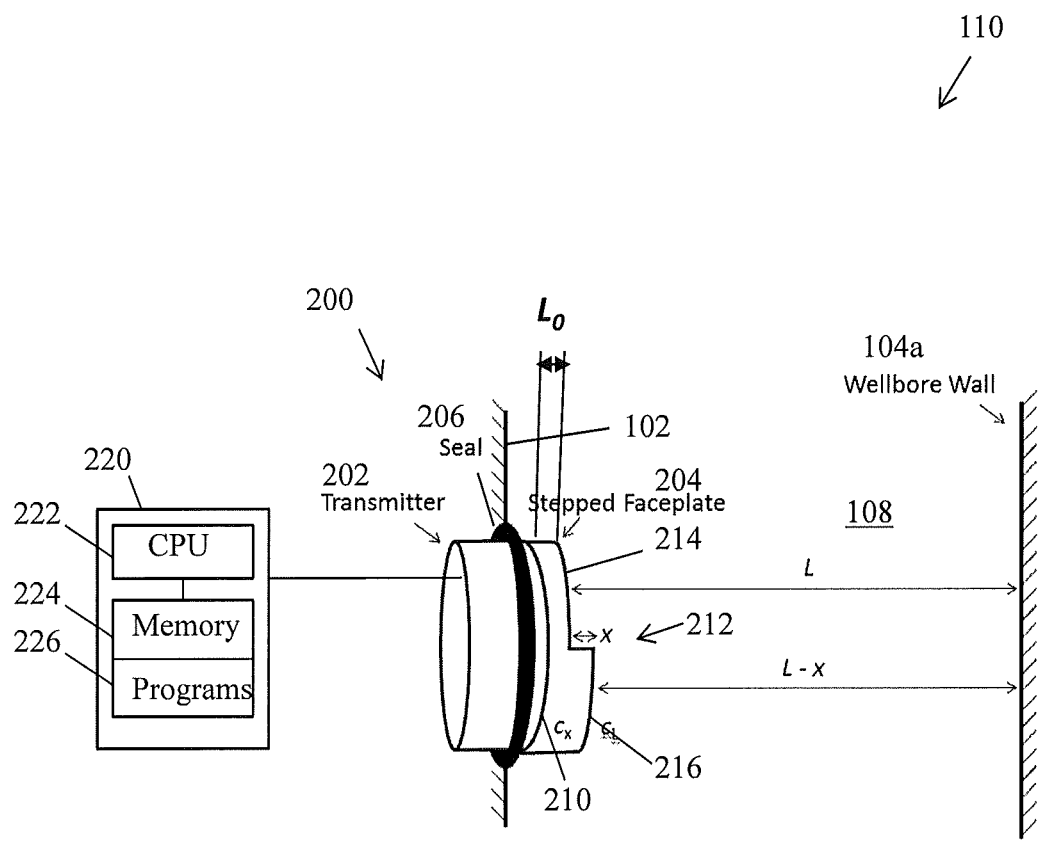
FIG. 2 shows a detailed view of the fluid testing apparatus of FIG. 1 in one embodiment.

FIG. 2 shows a detailed view of the fluid testing apparatus 110 of FIG. 1 in one embodiment. The fluid testing apparatus 110 includes an acoustic device 200 disposed on the member 102. The acoustic device 200 includes an acoustic transducer 202 and a faceplate 204, which may be a stepped faceplate, as described below. The faceplate 204 includes a first surface 210 and a second surface 212 that is opposite the first surface 210. The second surface 212 is a stepped surface, including a non-stepped face 214 and a stepped face 216. The distance between the non-stepped face 214 and the first surface 210 is less than the distance between the stepped face 216 and the first surface 210. As shown in FIG. 2, a perpendicular distance between the first surface 210 and the non-stepped face 214 is $L_0$ and a perpendicular distance between the first surface 210 and the stepped face 216 is $L_0+x$. Therefore, a perpendicular distance between the stepped face 216 and the non-stepped face 214 is x. In alternate embodiments, the second surface 212 may include more than two faces. The acoustic transducer 202 is coupled to the first face 210 of the faceplate 204 and transmits acoustic signals into the faceplate 204 and receives acoustic signals from the faceplate 204. A seal 206 between the acoustic device 200 and the member 102 prevents ingress of fluids into the member 102. As disposed on the member 102, the non-stepped face 214 is at a distance L from the wellbore wall 104a and stepped face 216 is at a distance L−x from the wellbore wall 104a.

The fluid testing apparatus 110 further includes a control unit 220 coupled to the acoustic transducer 202. The control unit 220 includes a processor 222 and a memory storage device 224. The memory storage device 224 may be any non-transitory computer-readable storage medium, such as a solid-state memory, ROM, RAM, etc. The memory storage device 224 includes a set of programs 226 stored therein. The programs 226 may include instructions that when read by the processor 222 enable the processor to, among other things, determine an acoustic property of the fluid 108 in the wellbore 104 based on measurements obtained from the acoustic device 200. The control unit 220 may further control an operation of the acoustic device 200 or, specifically, the acoustic transducer 202. The control unit 220 may be disposed downhole with the acoustic device 200 or may be situated at the surface location 120.

Figure 3:
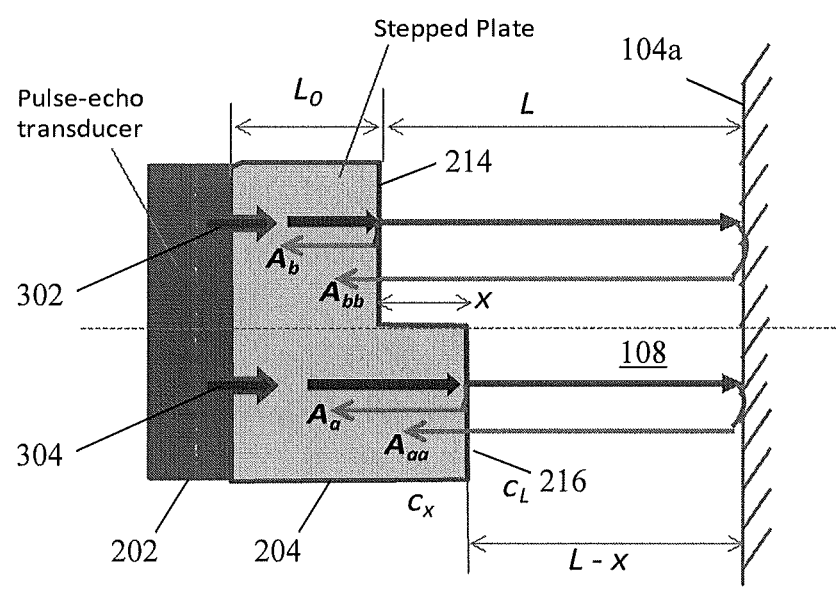
FIG. 3 shows various transmission and/or reflection paths for an acoustic pulse generated by an acoustic transducer of the fluid testing apparatus.

FIG. 3 shows various transmission and/or reflection paths for an acoustic pulse generated by the acoustic transducer 202 of the exemplary acoustic device 200 of the present disclosure. The acoustic transducer 202 transmits an original acoustic pulse or signal that enters through the faceplate 204 at first surface 210 and travels through the faceplate 204 to the second surface 212. The original acoustic pulse may includes a first portion 302 that intercepts the non-stepped face 214 and a second portion 304 that intercepts the stepped face 216. Reflection and transmission of the incident pulses occurs at each of the non-stepped face 214 and the stepped face 216.

For the first portion 302 impinging on non-stepped face 214, an internally reflected signal ($A_b$) may be reflected back through the faceplate 204 to the acoustic transducer 202. Another part of the first portion 302 is transmitted into the fluid 108 as indicated by signal $A_{bb}$. Signal $A_{bb}$ propagates through the fluid 108 to the wellbore wall 104a and is reflected from the wellbore wall 104a back through the fluid 108 to the non-stepped face 214. Signal $A_{bb}$ then passes through the non-stepped face 214 and propagates back to the acoustic transducer 202. For signals resulting from the first portion 302, the path length in the faceplate 204 is distance $L_0$ and the path length in the fluid 108 is distance L.

Similarly, for the second portion 304 impinging on the stepped face 216, an internally reflected signal $A_a$ may be reflected back through the faceplate 204 to the acoustic transducer 202. Another part of the first portion 302 is transmitted into the fluid 108 as indicated by signal $A_{aa}$. Signal $A_{aa}$ propagates through the fluid 108 to the wellbore wall 104a and is reflected from the wellbore wall 104a back through the fluid 108 to the stepped face 216. Signal $A_{aa}$ then passes through the stepped face 216 and propagates back to the acoustic transducer 202. For signals resulting from the second portion 304, the path length in the faceplate 204 is distance $L_0+x$ and the path length in the fluid 108 is distance L−x.

Signals propagating through the faceplate 204 travel at an acoustic velocity $c_X$. Signals propagating through the fluid 108 travel at an acoustic velocity $C_L$, also known as "mud velocity." The acoustic velocity $C_L$ may be an unknown value that is determined via the methods disclosed herein. The acoustic velocity $c_X$ either may be a known quantity or may be determined using the methods disclosed herein. A sudden drop in the mud velocity can indicate gas influx from the formation into the drilling mud.

Figure 4A:
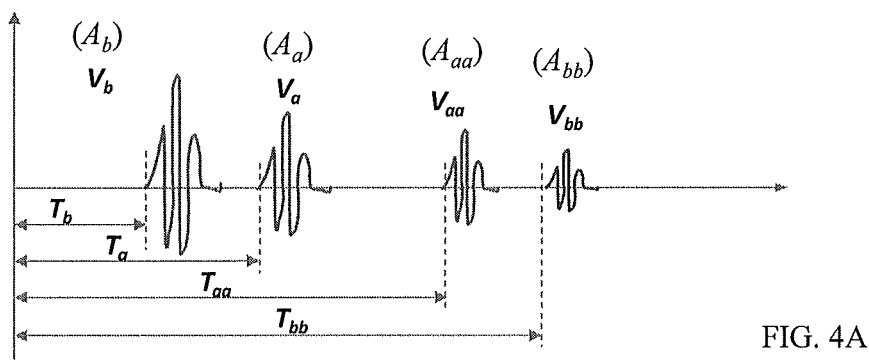
FIGS. 4A and 4B show schematic waveforms of the pulses received at the acoustic transducer.
Figure 4B:
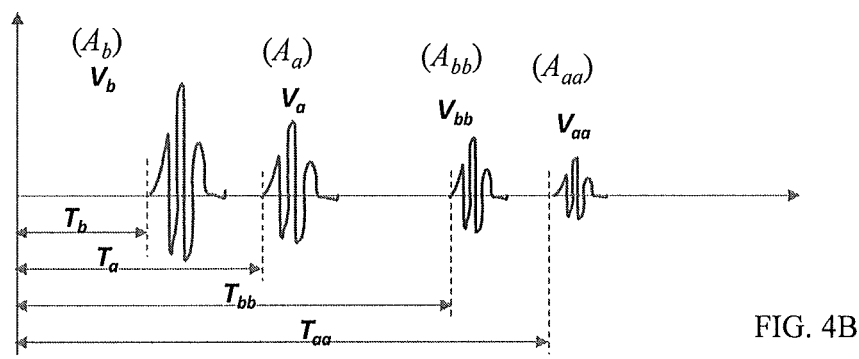

FIGS. 4A and 4B show measured waveforms ($V_a$, $V_b$, $V_{aa}$ and $V_{bb}$) of the respective pulses $A_a$, $A_b$, $A_{aa}$ and $A_{bb}$ (FIG. 3) received at the acoustic transducer 202. FIG. 4A shows the waveform measurements obtained when a velocity of sound ($C_X$) in the faceplate 204 is greater than a velocity of sound ($C_L$) in the fluid 108. The travel time for a selected pulse is a difference between a time at which the original acoustic pulse is generated at the acoustic transducer 202 and time at which the reflected pulse corresponding to the selected pulse is detected at the acoustic transducer 202. Pulse $A_a$ (traveling entirely within the faceplate 204) has a travel time $T_a$, pulse $A_b$ (traveling entirely within the faceplate 204) has a travel time $T_b$, pulse $A_{aa}$ (traveling within both the faceplate 204 and the fluid 108) has a travel time $T_{aa}$ and pulse $A_{bb}$ (traveling within both the faceplate 204 and the fluid 108) has a travel time $T_{bb}$. Since, pulses $A_a$ and $A_b$ are internally reflected, their travel times $T_a$ and $T_b$ are earlier that the travel times $T_{aa}$ and $T_{bb}$ of pulses $A_{aa}$ and $A_{bb}$, which travel through the fluid 108 and are reflected from the wellbore wall 104a. Since the pulse $A_{aa}$ spends more time in the faceplate 204 than pulse $A_{bb}$ and since $c_X > c_L$, pulse $A_{aa}$ arrives before pulse $A_{bb}$.

FIG. 4B shows the measurements obtained when a velocity of sound in the faceplate 204 ($c_X$) is less than a velocity of sound ($c_L$) in the fluid 108. For the internally reflected pulses $A_a$ and $A_b$, the travel times do not change. However, since pulse $A_{aa}$ spends more time in the faceplate 204 than pulse $A_{bb}$ and since $c_X < c_L$, pulse $A_{bb}$ arrives before pulse $A_{aa}$.

The equations for round-trip travel time for a selected reflected pulse may be written in equation form. The round-trip travel time is a function of a length of a path (path length) for the pulse in a particular medium (i.e., the faceplate 204 and/or the fluid 108) as well as the acoustic velocities (i.e., $c_X$ and/or $c_L$) of the particular medium. The equation for a round-trip travel time for signal $A_{aa}$ is:

$$T_{aa}=2(L_0+x)/c_x+2(L-x)/c_L \qquad \text{Eq. (1)}$$

The equation for a round-trip travel time for signal $A_{bb}$ is:

$$T_{bb}=2L_0/c_x+2L/c_L \qquad \text{Eq. (2)}$$

From Eqs. (1) and (2), the difference between travel times for signal $A_{aa}$ and signal $A_{bb}$ is $$T_{aa}-T_{bb}=2x(1/c_x-1/c_L) \qquad \text{Eq. (3)}$$

Since $T_{aa}$, $T_{bb}$ are measured quantities and x and $c_x$ are known quantities, the speed of sound of the fluid 108 in the wellbore 104 may be determined by solving Eq. (3) to obtain:

$$c_L=1/[1/c_x-(T_{aa}-T_{bb})/2x] \qquad \text{Eq. (4)}$$

Once the speed of sound in the fluid 108 in the wellbore 104 is known, a standoff L between the faceplate 204 from the wellbore wall 104a (or equivalently, between the member 102 and the wellbore wall 104a) may be determined as $$L=c_L T_{bb}/2-L_0/c_x \qquad \text{Eq. (5)}$$

In addition, the speed of sound ($c_x$) in the faceplate 204 may be determined from round-trip travel times of the internally reflected acoustic pulses (i.e., signals $A_a$ and $A_b$), as shown in Eqs. (6)-(8). The round-trip travel time for signal $A_a$ is:

$$T_a=2(L_0+x)/c_x \qquad \text{Eq. (6)}$$

and the round-trip travel time for signal $A_b$ is $$T_b=2L_0/c_x \qquad \text{(Eq. 7)}$$

From Eqs. (6) and (7), the speed of sound $c_X$ is determined as $$c_x=2x/(T_a-T_b) \qquad \text{Eq. (8)}$$

In another aspect of the present disclosure, acoustic attenuation coefficients of the faceplate 204 and of the fluid 108 may be determined. Additionally, an acoustic impedance of the fluid 108 may be determined. The amplitudes of the returned pulse waveforms ($V_a$, $V_b$, $V_{aa}$, and $V_{bb}$) are given by the following equations (9)-(12):

$$V_b = P_0 e^{-2a_x L_0} \frac{Z_f - Z_X}{Z_f + Z_X} \qquad \text{Eq. (9)}$$

$$V_a = P_0 e^{-2a_x (L_0+x)} \frac{Z_f - Z_X}{Z_f + Z_X} \qquad \text{Eq. (10)}$$

$$V_{bb} = P_0 e^{-2a_x L_0} \frac{4Z_f Z_X}{(Z_f + Z_X)^2} e^{-2a_f L} \frac{Z_c - Z_f}{Z_c + Z_f} \qquad \text{Eq. (11)}$$

$$V_{aa} = P_0 e^{-2a_x (L_0+x)} \frac{4Z_f Z_X}{(Z_f + Z_X)^2} e^{-2a_f (L-x)} \frac{Z_c - Z_f}{Z_c + Z_f} \qquad \text{Eq. (12)}$$

In Eqs. (9)-(12), $P_0$ is the amplitude of the original acoustic signal generated by the acoustic transducer 202, and $a_x$ and $a_f$ are the sound attenuation coefficient of the material of the face plate and the sound attenuation coefficient of the fluid 108, respectively. $Z_f$, $Z_X$ and $Z_C$ are the acoustic impedances of the fluid, the material of the faceplate 204 and the material of the borehole wall (or of the casing), respectively.

The attenuation coefficient of the face plate ($a_x s$) may be determined from Eq. (9) and Eq. (10), to obtain:

$$a_x = -\frac{1}{2x}\ln\left(\frac{V_b}{V_a}\right) \qquad \text{Eq. (13)}$$

The attenuation coefficient of the fluid ($a_f$) may be determined from Eq. (11) and Eq. (12) and the determined coefficient $a_x$ from Eq. (13) to obtain:

$$a_f = a_x - \frac{1}{2x}\ln\left(\frac{V_{bb}}{V_{aa}}\right) \qquad \text{Eq. (14)}$$

By taking the ratio of $V_{bb}$ (Eq. (11)) and $V_b$ (Eq. (9)), the following Eq. (15) is obtained:

$$\frac{V_{bb}}{V_b} = \frac{4Z_f Z_X}{Z_f^2 - Z_X^2} e^{-2a_f L} \frac{Z_c - Z_f}{Z_c + Z_f} \qquad \text{Eq. (15)}$$

The fluid impedance $Z_f$ may then be solved from Eq. (15). $Z_C$ is a known acoustic impedance of the material (e.g., steel casing) of the wellbore wall 104a. $Z_X$ is an acoustic impedance of the material of the faceplate 204, which is either known or may be determined from Eq. (13), L is the standoff distance (determined in Eq. (5)) and $a_f$ is the fluid attenuation coefficient, determined in Eq. (14). Moreover, the density of the fluid may be then estimated by $p_f = Z_f/c_L$.

Therefore, in one aspect, the present disclosure provides a method of determining an acoustic property of a fluid in a wellbore, the method including: placing a faceplate in the wellbore with a stepped surface of the faceplate in contact with the fluid, wherein the stepped surface includes a non-stepped face and a stepped face; transmitting an acoustic pulse through the faceplate into the fluid, wherein a first portion of the acoustic pulse passes from the faceplate into the fluid via the non-stepped face and a second portion of the acoustic pulse passes from the faceplate into the fluid via the stepped face; receiving a first reflected acoustic pulse related to the first portion of the acoustic pulse from a wellbore surface and a second reflected acoustic pulse related to the second portion of the acoustic pulse from the wellbore surface; obtaining a measurement of the first reflected acoustic pulse and a measurement of the second reflected pulse; and determining from the obtained measurements the acoustic property of the fluid in the wellbore. In one embodiment, a path of the first reflected acoustic pulse intersects the non-stepped face of the faceplate and a path of the second reflected acoustic pulse intersects the stepped face of the faceplate. When the acoustic property of the fluid is an acoustic velocity of the fluid, the method determines the acoustic velocity of the fluid using a difference between a travel time of the first reflected signal and a travel time of the second reflected signal. The difference between the travel time of the first reflected signal and the travel time of the second reflected signal is related to a difference between a path length through the fluid of the first reflected signal and a path length through the fluid of the second reflected signal. Additionally, a standoff distance between the faceplate and the wellbore surface may be determined using the determined acoustic velocity of the fluid. When the acoustic property of the fluid is an acoustic attenuation of the fluid, the acoustic attenuation of the fluid may be determined from an amplitude of the first reflected signal an amplitude of the second reflected signal. The method may further include determining an acoustic impedance of the fluid using the determined acoustic attenuation of the fluid.

In another aspect, the present disclosure provides an apparatus for determining an acoustic property of a fluid in a wellbore, the apparatus including: a faceplate having a stepped surface that includes a non-stepped face and a stepped face, wherein the stepped surface is coupled to the fluid in the wellbore; an acoustic transducer configured to transmit an acoustic signal to pass through the stepped surface of the faceplate into the fluid, wherein a first portion of the transmitted acoustic signal passes from the faceplate into the fluid via the non-stepped face and a second portion of the acoustic pulse passes from the faceplate into the fluid via the stepped face; and a processor configured to: receive measurements of a first reflected pulse related to reflection of the first portion of the transmitted acoustic signal from a wellbore surface a second reflected pulse related to reflection of the second portion of the transmitted acoustic signal from the wellbore surface, and determine the acoustic property of the fluid in the wellbore from the received measurements of the first reflected acoustic pulse and the second reflected acoustic pulse. In one embodiment, a path of the first reflected signal intersects the non-stepped face a path of the second reflected acoustic pulse intersects the stepped face. When the acoustic property of the fluid is an acoustic velocity of the fluid, the processor may determine the acoustic velocity of the fluid from a difference between a travel time of the first reflected signal and a travel time of the second reflected signal. The processor may further determine a standoff distance between a member and the wellbore surface using the determined acoustic velocity for the faceplate disposed on the member. A difference between the travel time of the first reflected signal and the travel time of the second reflected signal is related to a difference in a path length of the first reflected signal through the fluid and a path length of the second reflected signal through the fluid. When the acoustic property of the fluid is attenuation of an acoustic signal in the fluid, the processor may determine the attenuation of the acoustic signal in the fluid using an amplitude of the first signal and an amplitude of the second signal. The processor may further determine an acoustic impedance of the fluid using the determined acoustic attenuation of the fluid.

In yet another aspect, the present disclosure provides a system for determining an acoustic property of a fluid in a wellbore, the system including: a member disposed in the wellbore; a faceplate disposed on the member, the faceplate having a stepped surface coupled to the fluid in the wellbore, wherein the stepped surface includes a non-stepped face and a stepped face; an acoustic transducer configured to transmit an acoustic signal into the faceplate, wherein a first portion of the transmitted acoustic signal passes from the faceplate into the fluid through the non-stepped face and a second portion of the transmitted acoustic signal passes from the faceplate into the fluid through the stepped face, the acoustic transducer further configured to receive a first reflected acoustic signal related reflection of the first portion of the transmitted acoustic signal from a surface of the wellbore and a second reflected acoustic signal related to reflection of the second portion of the transmitted acoustic signal from the surface of the wellbore; and a processor configured to: receive measurements of the first reflected pulse and the second reflected pulse from the acoustic transducer, and determine the acoustic property of the fluid in the wellbore from the received measurements of the first reflected acoustic pulse and the second reflected acoustic pulse. In one embodiment, a path of the first reflected acoustic pulse intersects the non-stepped face and a path of the second reflected acoustic pulse intersects the stepped face. When the acoustic property of the fluid is an acoustic velocity of the fluid, the processor may determine the acoustic velocity of the fluid from a difference between measured travel times of the first reflected signal and the second reflected signal. The processor may further determine a standoff distance between the member and the wellbore surface. When the acoustic property of the fluid is attenuation of an acoustic signal in the fluid, the processor may determine the attenuation of the acoustic signal in the fluid using an amplitude of the first signal and an amplitude of the second signal. The processor may further determine an acoustic impedance of the fluid using the determined acoustic attenuation of the fluid.

While the disclosure has been described with reference to an exemplary embodiment or embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the claims.

What is claimed is:

1. A method of determining an acoustic property of a fluid in a wellbore, comprising:
   placing a faceplate in the wellbore with a stepped surface of the faceplate in contact with the fluid, wherein the stepped surface includes a non-stepped face and a stepped face;
   transmitting an acoustic pulse through the faceplate into the fluid, wherein a first portion of the acoustic pulse passes from the faceplate into the fluid via the non-stepped face and a second portion of the acoustic pulse passes from the faceplate into the fluid via the stepped face;
   receiving a first reflected acoustic pulse related to the first portion of the acoustic pulse from a wellbore surface and a second reflected acoustic pulse related to the second portion of the acoustic pulse from the wellbore surface;
   obtaining a measurement of the first reflected acoustic pulse and a measurement of the second reflected pulse; and
   determining from the obtained measurements the acoustic property of the fluid in the wellbore.

2. The method of claim 1, wherein a path of the first reflected acoustic pulse intersects the non-stepped face of the faceplate and a path of the second reflected acoustic pulse intersects the stepped face of the faceplate.

3. The method of claim 1, wherein the acoustic property of the fluid further comprises an acoustic velocity of the fluid, further comprising determining the acoustic velocity of the fluid using a difference between a travel time of the first reflected signal and a travel time of the second reflected signal.

4. The method of claim 3, wherein the difference between the travel time of the first reflected signal and the travel time of the second reflected signal is related to a difference between a path length through the fluid of the first reflected signal and a path length through the fluid of the second reflected signal.

5. The method of claim 3, further comprising determining a standoff distance between the faceplate and the wellbore surface using the determined acoustic velocity of the fluid.

6. The method of claim 1, wherein the acoustic property of the fluid further comprises acoustic attenuation of the fluid, further comprising determining the acoustic attenuation of the fluid from an amplitude of the first reflected signal an amplitude of the second reflected signal.

7. The method of claim 6, further comprising determining an acoustic impedance of the fluid using the determined acoustic attenuation of the fluid.

8. An apparatus for determining an acoustic property of a fluid in a wellbore, comprising:
  a faceplate having a stepped surface that includes a non-stepped face and a stepped face, wherein the stepped surface is coupled to the fluid in the wellbore;
  an acoustic transducer configured to transmit an acoustic signal to pass through the stepped surface of the faceplate into the fluid, wherein a first portion of the transmitted acoustic signal passes from the faceplate into the fluid via the non-stepped face and a second portion of the acoustic pulse passes from the faceplate into the fluid via the stepped face; and
  a processor configured to:
  receive measurements of a first reflected pulse related to reflection of the first portion of the transmitted acoustic signal from a wellbore surface a second reflected pulse related to reflection of the second portion of the transmitted acoustic signal from the wellbore surface, and
  determine the acoustic property of the fluid in the wellbore from the received measurements of the first reflected acoustic pulse and the second reflected acoustic pulse.

9. The apparatus of claim 8, wherein a path of the first reflected signal intersects the non-stepped face a path of the second reflected acoustic pulse intersects the stepped face.

10. The apparatus of claim 8, wherein the acoustic property of the fluid further comprising an acoustic velocity of the fluid and the processor is further configured to determine the acoustic velocity of the fluid from a difference between a travel time of the first reflected signal and a travel time of the second reflected signal.

11. The apparatus of claim 10, wherein the faceplate is disposed on a member in the wellbore, further comprising determining a standoff distance between the member and the wellbore surface using the determined acoustic velocity.

12. The apparatus of claim 10, wherein a difference between the travel time of the first reflected signal and the travel time of the second reflected signal is related to a difference in a path length of the first reflected signal through the fluid and a path length of the second reflected signal through the fluid.

13. The apparatus of claim 8, wherein the acoustic property of the fluid further comprises attenuation of an acoustic signal in the fluid and the processor is further configured to determine the attenuation of the acoustic signal in the fluid using an amplitude of the first signal and an amplitude of the second signal.

14. The apparatus of claim 13, wherein the processor is further configured to determine an acoustic impedance of the fluid using the determined acoustic attenuation of the fluid.

15. A system for determining an acoustic property of a fluid in a wellbore, comprising:
  a member disposed in the wellbore;
  a faceplate disposed on the member, the faceplate having a stepped surface coupled to the fluid in the wellbore, wherein the stepped surface includes a non-stepped face and a stepped face;
  an acoustic transducer configured to transmit an acoustic signal into the faceplate, wherein a first portion of the transmitted acoustic signal passes from the faceplate into the fluid through the non-stepped face and a second portion of the transmitted acoustic signal passes from the faceplate into the fluid through the stepped face, the acoustic transducer further configured to receive a first reflected acoustic signal related reflection of the first portion of the transmitted acoustic signal from a surface of the wellbore and a second reflected acoustic signal related to reflection of the second portion of the transmitted acoustic signal from the surface of the wellbore; and
  a processor configured to:
  receive measurements of the first reflected pulse and the second reflected pulse from the acoustic transducer, and
  determine the acoustic property of the fluid in the wellbore from the received measurements of the first reflected acoustic pulse and the second reflected acoustic pulse.

16. The system of claim 15, wherein a path of the first reflected acoustic pulse intersects the non-stepped face and a path of the second reflected acoustic pulse intersects the stepped face.

17. The system of claim 15, wherein acoustic property of the fluid further comprising an acoustic velocity of the fluid and the processor is further configured to determine the acoustic velocity of the fluid from a difference between measured travel times of the first reflected signal and the second reflected signal.

18. The system of claim 17, further comprising determining a standoff distance between the member and the wellbore surface.

19. The system of claim 15, wherein the acoustic property of the fluid further comprises attenuation of an acoustic signal in the fluid and the processor is further configured to determine the attenuation of the acoustic signal in the fluid using an amplitude of the first signal and an amplitude of the second signal.

20. The system of claim 19, wherein the processor is further configured to determine an acoustic impedance of the fluid using the determined acoustic attenuation of the fluid.

* * * * *